United States Patent
Grostefon et al.

(10) Patent No.: US 11,076,960 B2
(45) Date of Patent: *Aug. 3, 2021

(54) CONSTRAINED MOBILE BEARING HIP ASSEMBLY AND METHOD

(71) Applicant: DePuy Synthes Products, Inc., Raynham, MA (US)

(72) Inventors: Justin D. Grostefon, Columbia City, IN (US); Matthew T. Block, Carmel, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 107 days.

This patent is subject to a terminal disclaimer.

(21) Appl. No.: 16/437,944

(22) Filed: Jun. 11, 2019

(65) Prior Publication Data

US 2019/0290442 A1    Sep. 26, 2019

Related U.S. Application Data

(60) Continuation of application No. 15/646,286, filed on Jul. 11, 2017, now Pat. No. 10,314,711, which is a
(Continued)

(51) Int. Cl.
*A61F 2/32* (2006.01)
*A61F 2/34* (2006.01)
(Continued)

(52) U.S. Cl.
CPC .................. *A61F 2/32* (2013.01); *A61F 2/34* (2013.01); *A61F 2/36* (2013.01);
(Continued)

(58) Field of Classification Search
CPC ...... A61F 2/32; A61F 2/34; A61F 2/36; A61F 2002/30364; A61F 2002/30367;
(Continued)

(56) References Cited

U.S. PATENT DOCUMENTS 3,510,883 A    5/1970    Cathcart
3,641,590 A    2/1972    Michele
(Continued)

FOREIGN PATENT DOCUMENTS

CN    201208317 Y    3/2009
DE       2139878 A1    2/1973
(Continued)

OTHER PUBLICATIONS

International Search Report, International Application No. PCT/US2013/40107, dated Jun. 12, 2013, 11 pages.
(Continued)

*Primary Examiner* — Dinah Baria

(74) *Attorney, Agent, or Firm* — Barnes & Thornburg LLP

(57) ABSTRACT

An acetabular hip implant and method includes an acetabular shell component having a first feature and a first insert having a second feature that cooperates with the first feature of the acetabular shell component and further includes a third feature. The implant further includes a second insert having a fourth feature that cooperates with the third feature of the first insert and further includes a fifth feature. A femoral head component includes a sixth feature that cooperates with the fifth feature. Interaction between the first and second features, between the third and fourth features, and between the fifth and sixth features mechanically constrains the acetabular hip implant to prevent dislocation of the femoral head during rotation.

18 Claims, 6 Drawing Sheets

Related U.S. Application Data continuation of application No. 15/005,583, filed on Jan. 25, 2016, now Pat. No. 9,700,416, which is a continuation of application No. 14/513,171, filed on Oct. 13, 2014, now Pat. No. 9,241,799, which is a division of application No. 13/529,021, filed on Jun. 21, 2012, now Pat. No. 8,858,645.

(51) Int. Cl.
  *A61F 2/36* (2006.01)
  *A61F 2/30* (2006.01)

(52) U.S. Cl.
  CPC .......... *A61F 2002/305* (2013.01); *A61F 2002/30364* (2013.01); *A61F 2002/30367* (2013.01); *A61F 2002/30397* (2013.01); *A61F 2002/30652* (2013.01); *A61F 2002/30654* (2013.01); *A61F 2002/30662* (2013.01); *A61F 2002/30827* (2013.01); *A61F 2002/30934* (2013.01); *A61F 2002/3208* (2013.01); *A61F 2002/3216* (2013.01); *A61F 2002/3233* (2013.01); *A61F 2002/345* (2013.01); *A61F 2002/3448* (2013.01); *F04C 2270/0421* (2013.01)

(58) Field of Classification Search
  CPC .. A61F 2002/30827; A61F 2002/30662; A61F 2002/30934; A61F 2002/3208; A61F 2002/3216; A61F 2002/3233; A61F 2002/3448; A61F 2002/345
  See application file for complete search history.

(56) References Cited

U.S. PATENT DOCUMENTS

| | | |
|---|---|---|
| 3,656,184 A | 4/1972 | Chambers |
| 3,683,421 A | 8/1972 | Martinie |
| 3,869,730 A | 3/1975 | Skobel |
| 3,891,997 A | 7/1975 | Herbert |
| 3,925,824 A | 12/1975 | Freeman |
| 4,024,588 A | 5/1977 | Janssen et al. |
| 4,032,994 A | 7/1977 | Frey |
| 4,068,324 A | 1/1978 | Townley et al. |
| 4,318,191 A | 3/1982 | Tepic |
| 4,532,660 A | 8/1985 | Field |
| 4,795,469 A | 1/1989 | Oh |
| 4,795,470 A | 1/1989 | Goymann et al. |
| 4,878,916 A | 11/1989 | Rhenter et al. |
| 4,911,723 A | 3/1990 | Menschik |
| 4,955,919 A | 9/1990 | Pappas et al. |
| 4,960,427 A | 10/1990 | Noiles |
| 5,009,665 A | 4/1991 | Serbousek et al. |
| 5,047,062 A | 9/1991 | Pappas et al. |
| 5,326,368 A | 7/1994 | Collazo |
| 5,370,703 A | 12/1994 | Willert et al. |
| 5,431,657 A | 7/1995 | Rohr |
| 5,549,698 A | 8/1996 | Averill et al. |
| 5,553,476 A | 9/1996 | Oehy et al. |
| 5,593,447 A | 1/1997 | Angeli |
| 5,676,704 A | 10/1997 | Ries et al. |
| 5,702,474 A | 12/1997 | McCandliss |
| 5,824,108 A | 10/1998 | Huebner |
| 5,879,405 A | 3/1999 | Ries et al. |
| 5,888,207 A | 3/1999 | Nieder et al. |
| 5,951,605 A | 9/1999 | Dennis et al. |
| 6,002,859 A | 12/1999 | Digioia, III et al. |
| 6,066,176 A | 5/2000 | Oshida |
| 6,093,208 A | 7/2000 | Tian |
| 6,120,545 A | 9/2000 | Hamelijnck et al. |
| 6,126,695 A | 10/2000 | Semlitsch |
| 6,152,961 A | 11/2000 | Ostiguy, Jr. et al. |
| 6,200,350 B1 | 3/2001 | Masini |
| 6,206,929 B1 | 3/2001 | Ochoa et al. |
| 6,224,633 B1 | 5/2001 | Kalberer et al. |
| 6,248,132 B1 | 6/2001 | Harris |
| 6,258,097 B1 | 7/2001 | Cook et al. |
| 6,447,550 B1 | 9/2002 | Hunter et al. |
| 6,488,715 B1 | 12/2002 | Pope et al. |
| 6,503,281 B1 | 1/2003 | Mallory |
| 6,537,321 B1 | 3/2003 | Horber |
| 6,641,617 B1 | 11/2003 | Merrill et al. |
| 6,682,566 B2 | 1/2004 | Draenert |
| 6,726,725 B2 | 4/2004 | Hunter et al. |
| 7,004,972 B2 | 2/2006 | Yoon |
| 7,044,974 B2 | 5/2006 | Garber et al. |
| 7,108,720 B2 | 9/2006 | Hanes |
| 7,115,145 B2 | 10/2006 | Richards |
| 7,179,298 B2 | 2/2007 | Greenlee |
| 7,211,113 B2 | 5/2007 | Zelener et al. |
| 7,335,231 B2 | 2/2008 | McLean |
| 7,455,694 B2 | 11/2008 | Epaules et al. |
| 7,470,287 B2 | 12/2008 | Tornier et al. |
| 7,494,509 B1 | 2/2009 | Hershberger et al. |
| 7,572,296 B2 | 8/2009 | Scott et al. |
| 7,682,398 B2 | 3/2010 | Croxton et al. |
| 7,794,504 B2 | 9/2010 | Case |
| 7,985,261 B2 | 7/2011 | Masini |
| 8,177,850 B2 | 5/2012 | Rudan et al. |
| 8,211,183 B2 | 7/2012 | Podolsky |
| 8,211,184 B2 | 7/2012 | Ries et al. |
| 8,268,383 B2 | 9/2012 | Langhorn |
| 8,398,718 B2 | 3/2013 | Richardson et al. |
| 8,465,549 B2 | 6/2013 | Richardson |
| 8,771,366 B2 | 7/2014 | Whitaker et al. |
| 8,858,645 B2 | 10/2014 | Grostefon et al. |
| 9,066,803 B2 | 6/2015 | Whitaker et al. |
| 9,241,799 B2 | 1/2016 | Grostefon et al. |
| 9,393,122 B2 | 7/2016 | Whitaker et al. |
| 9,700,416 B2 | 7/2017 | Grostefon et al. |
| 10,314,711 B2 | 6/2019 | Grostefon et al. |
| 2003/0171817 A1 | 9/2003 | Rambert et al. |
| 2003/0212459 A1 | 11/2003 | Gibbs |
| 2003/0236572 A1 | 12/2003 | Bertram, III |
| 2004/0078083 A1 | 4/2004 | Gibbs et al. |
| 2004/0143341 A1 | 7/2004 | McLean |
| 2004/0193282 A1 | 9/2004 | Hanes |
| 2004/0204767 A1 | 10/2004 | Park et al. |
| 2004/0225371 A1 | 11/2004 | Roger |
| 2005/0096748 A1 | 5/2005 | Yoon |
| 2005/0261776 A1 | 11/2005 | Taylor |
| 2006/0167556 A1 | 7/2006 | Lazennec et al. |
| 2006/0206211 A1 | 9/2006 | Daniels et al. |
| 2006/0217815 A1 | 9/2006 | Gibbs et al. |
| 2007/0100447 A1 | 5/2007 | Steinberg |
| 2007/0106389 A1 | 5/2007 | Croxton et al. |
| 2007/0225818 A1 | 9/2007 | Reubelt et al. |
| 2008/0015707 A1 | 1/2008 | Lambert et al. |
| 2008/0114459 A1 | 5/2008 | Scott et al. |
| 2008/0177395 A1 | 7/2008 | Stinnette |
| 2008/0208350 A1 | 8/2008 | Roger |
| 2008/0294258 A1 | 11/2008 | Revie et al. |
| 2009/0018666 A1 | 1/2009 | Grundei et al. |
| 2009/0088866 A1 | 4/2009 | Case |
| 2009/0093887 A1 | 4/2009 | Walter et al. |
| 2009/0105714 A1 | 4/2009 | Kozak |
| 2009/0171464 A1 | 7/2009 | Imhof |
| 2009/0192610 A1 | 7/2009 | Case et al. |
| 2009/0204225 A1 | 8/2009 | Meridew et al. |
| 2009/0259317 A1 | 10/2009 | Steinberg |
| 2009/0281545 A1 | 11/2009 | Stubbs |
| 2009/0287311 A1 | 11/2009 | Preuss et al. |
| 2010/0261998 A1 | 10/2010 | Stiehl |
| 2011/0032184 A1 | 2/2011 | Roche et al. |
| 2011/0054628 A1 | 3/2011 | Banks et al. |
| 2012/0029651 A1 | 2/2012 | Ashton et al. |
| 2012/0065737 A1 | 3/2012 | Chow |
| 2012/0109327 A1 | 5/2012 | Forsell |
| 2012/0209397 A1 | 8/2012 | Richardson |
| 2012/0209398 A1 | 8/2012 | Richardson et al. |
| 2012/0221115 A1 | 8/2012 | Komistek |
| 2013/0158557 A1 | 6/2013 | Komistek |

(56) References Cited

U.S. PATENT DOCUMENTS

| | | |
|---|---|---|
| 2013/0158674 A1 | 6/2013 | Chow et al. |
| 2013/0165938 A1 | 6/2013 | Chow et al. |
| 2013/0304225 A1 | 11/2013 | Komistek |

FOREIGN PATENT DOCUMENTS

| | | |
|---|---|---|
| DE | 3643815 A1 | 6/1988 |
| DE | 10212982 A1 | 10/2003 |
| EP | 524857 A1 | 1/1993 |
| EP | 648478 A2 | 4/1995 |
| EP | 649640 A2 | 4/1995 |
| EP | 797964 A1 | 10/1997 |
| EP | 867158 A2 | 9/1998 |
| EP | 1508315 A2 | 2/2005 |
| EP | 1574183 A1 | 9/2005 |
| FR | 2357235 A1 | 2/1978 |
| FR | 2785523 A1 | 5/2000 |
| FR | 2889446 A1 | 2/2007 |
| GB | 1573608 A | 8/1980 |
| RU | 2042345 C1 | 8/1995 |
| RU | 2116769 C1 | 8/1998 |
| WO | 9615735 A1 | 5/1996 |
| WO | 9834567 A1 | 8/1998 |
| WO | 0064384 A1 | 11/2000 |
| WO | 0155476 A1 | 8/2001 |
| WO | 2006084426 A2 | 8/2006 |
| WO | 2008058756 A2 | 5/2008 |
| WO | 2009060006 A1 | 5/2009 |
| WO | 2009106816 A1 | 9/2009 |
| WO | 2009118673 A1 | 10/2009 |

OTHER PUBLICATIONS

International Search Report, International Application No. PCT/US2012/026492, dated Aug. 31, 2012, 16 pages.

English translation, Office Action for Japanese Patent Application No. 2013-555594 dated Nov. 24, 2015, 3 pages.

Patent Cooperation Treaty International Search Report, International Application No. PCT/US2013/033117 dated Jul. 1, 2013, 5 pages.

Transmittal of Chinese Search Report for Chinese Application No. 201310250315.7, dated Mar. 9, 2016, 2 pages.

Extended European Search Report, European Application No. 13173058.2-1654, dated Oct. 10, 2013, 8 pages.

ular projection that is movably secured within the at least
CONSTRAINED MOBILE BEARING HIP ASSEMBLY AND METHOD This application is a continuation of U.S. patent application Ser. No. 15/646,286 filed on Jul. 11, 2017, now U.S. Pat. No. 10,314,711, which is a continuation of U.S. patent application Ser. No. 15/005,583 filed on Jan. 25, 2016, now U.S. Pat. No. 9,700,416, which is a continuation of U.S. patent application Ser. No. 14/513,171 filed on Oct. 13, 2014, now U.S. Pat. No. 9,241,799, which is a divisional application of U.S. patent application Ser. No. 13/529,021 filed on Jun. 21, 2012, now U.S. Pat. No. 8,858,645, the entireties of each of which are hereby incorporated by reference.

TECHNICAL FIELD

The present disclosure relates generally to prosthetic orthopaedic implants, and more particular, to orthopaedic hip implants.

BACKGROUND

Many orthopaedic procedures involve the implantation of prosthetic devices to replace badly damaged or diseased joint tissue. Common orthopaedic procedures that involve prosthetic devices include total or partial hip, knee, and shoulder replacements. Hip replacement involves total or partial replacement of the hip ball and socket joint.

A total hip replacement procedure typically involves the implantation of two main component systems: a femoral component and an acetabular component. The femoral component includes a rigid stem that is anchored within the patient's femur and also includes a head that replaces the patient's natural femoral head. The acetabular component is implanted within the acetabulum of the patient and serves as a bearing surface for the head of the femoral component. The acetabular component generally includes an outer shell configured to engage the acetabulum of the patient and an inner bearing or liner coupled to the shell and configured to engage the femoral head. The femoral head and inner liner of the acetabular component form a ball and socket joint that approximates the natural hip joint.

SUMMARY

According to an illustrative embodiment, an acetabular hip implant includes an acetabular shell component configured to be implanted within an acetabulum of a patient, the acetabular shell component having a first feature defined in its inner surface, and a first insert secured to the acetabular shell component such that an outer surface of the first surface contacts the inner surface of the acetabular shell.

The first insert includes a second feature defined in its outer surface which contacts the first feature defined in the inner surface of the acetabular shell such that the first insert is permitted to rotate relative to the acetabular shell component about a first axis and prevented from rotating relative to the acetabular shell component about a second axis and a third axis.

The first insert having a third feature defined in its inner surface. A second insert is secured to the first insert such that the outer surface of the second insert contacts the inner surface of the first insert, the second insert having a fourth feature defined in its outer surface that contacts the third feature defined in the inner surface of the first insert. In this manner, the second insert is permitted to rotate relative to the first insert about the second axis and prevented from rotating relative to the first insert about the first axis and the third axis The second insert includes a fifth feature defined in its inner surface. A femoral head configured to be secured to a femoral stem is secured to the second insert such that the outer surface of the femoral head contacts the inner surface of the second insert. The femoral head includes a sixth feature defined in its outer surface which contacts the fifth feature defined in the inner surface of the second insert such that the femoral head is permitted to rotate relative to the second insert about the third axis and prevented from rotating relative to the second insert about the first axis and the second axis.

Interaction between the first and second features, between the third and fourth features, and between the fifth and sixth features mechanically constrains the acetabular hip implant to prevent dislocation of the femoral head during rotation.

The first feature is different than the second feature, the third feature is different than the fourth feature, and the fifth feature is different than the sixth feature.

One of the first and second features comprises at least one annular or semi-annular groove and the other of the first and second features comprises at least one annular or semi-annular projection that is movably secured within the at least one annular or semi-annular groove to permit rotation of the first insert with respect to the acetabular shell about only the first axis.

The at least one semi-annular groove includes two semi-annular grooves centered around the first axis and disposed on opposite sides of the acetabular shell or the first insert. The at least one semi-annular projection includes two semi-annular projections centered around the first axis and disposed on opposite sides of the other of the acetabular shell and the first insert.

One of the third and fourth features comprises at least one annular or semi-annular groove and the other of the third and fourth features comprises at least one annular or semi-annular projection that is movably secured within the at least one annular or semi-annular groove to permit rotation of the second insert with respect to the first insert about only the second axis.

The at least one semi-annular groove includes two semi-annular grooves centered around the second axis and disposed on opposite sides of the first or second insert. The at least one semi-annular projection includes two semi-annular projections centered around the second axis and disposed on opposite sides of the other of the first and second inserts.

One of the fifth and sixth features comprises an annular groove and the other of the fifth and sixth features comprises an annular projection that is movably secured within the annular groove to permit rotation of the femoral head with respect to the second insert about only the third axis.

The annular projection and the annular groove are centered around and symmetrical about the third axis.

The annular projection and the annular groove are offset from diameters of the second insert and the femoral head.

The first axis is orthogonal to the second axis and the third axis and the second axis is orthogonal to the third axis.

One of the first and second features comprises a semi-circular groove and the other of the first and second features comprises a semi-circular projection that is movably secured within the semi-circular groove to permit rotation of the first insert with respect to the acetabular shell about only the first axis.

The first feature includes two semi-circular projections disposed on opposite sides of the acetabular shell and the second feature includes two semi-circular grooves disposed on opposite sides of the first insert. The projections and grooves are centered about the first axis to allow for rotation about the first axis.

One of the third and fourth features comprises a semi-circular groove and the other of the third and fourth features comprises a semi-circular projection that is movably secured within the semi-circular groove to permit rotation of the second insert with respect to the first insert about only the second axis.

The third feature includes two semi-circular projections disposed on opposite sides of the first insert and the fourth feature includes two semi-circular grooves disposed on opposite sides of the second insert.

The projections and grooves are centered about the second axis to allow for rotation about the second axis.

According to a further illustrative embodiment, an acetabular hip implant comprises an acetabular shell component configured to be implanted within an acetabulum of a patient, the acetabular shell component having a first set of projections or grooves defined within an inner surface of the acetabular shell. A first insert is secured to the acetabular shell component such that the outer surface of the first surface contacts the inner surface of the acetabular shell.

The first insert includes a second set of projections or grooves defined within an outer surface of the first insert and cooperating with the first set of projections or grooves defined within the inner surface of the acetabular shell. In this manner, the first insert is permitted to rotate relative to the acetabular shell component about a first axis.

The first insert includes a third set of projections or grooves defined within an inner surface of the first insert. A second insert is secured to the first insert such that the outer surface of the second insert contacts the inner surface of the first insert. The second insert includes a fourth set of projections or grooves defined in its outer surface which cooperate with the third set of projections or grooves defined in the inner surface of the first insert such that the second insert is permitted to rotate relative to the first insert about the second axis.

The second insert includes a first annular projection or groove defined in its inner surface. A femoral head is configured to be secured to a femoral stem and the femoral head is secured to the second insert such that the outer surface of the femoral head contacts the inner surface of the second insert. The femoral head includes a second annular projection or groove defined in its outer surface which cooperates with the first annular projection or groove defined in the inner surface of the second insert. The femoral head is permitted to rotate relative to the second insert about the third axis; The first annular projection or groove and second annular projection or groove mechanically constrain the femoral head within the second insert to prevent dislocation of the femoral head during rotation.

The first set of projections or grooves includes two semi-annular projections centered around the first axis and disposed on opposite sides of the acetabular shell. The second set of projections or grooves includes two semi-annular grooves centered around the first axis and disposed on opposite sides of the first insert. The semi-annular projections of the first set and semi-annular grooves of the second set are configured to cooperate to allow rotation of the first insert about the first axis.

The third set of projections or grooves includes two semi-annular projections centered around the second axis and disposed on opposite sides of the first insert. The fourth set of projections or grooves includes two semi-annular grooves centered around the second axis and disposed on opposite sides of the second insert. The semi-annular projections of the third set and semi-annular grooves of the fourth set are configured to cooperate to allow rotation of the second insert about the second axis.

The first and second annular projections or grooves are centered around and symmetrical about the third axis and are offset from diameters of the second insert and the femoral head.

The first set of projections or grooves includes two semi-circular projections centered around the first axis and disposed on opposite sides of the acetabular shell. The second set of projections or grooves includes two semi-circular grooves centered around the first axis and disposed on opposite sides of the first insert. The semi-circular projections of the first set and semi-circular grooves of the second set are configured to cooperate to allow rotation of the first insert about the first axis.

The third set of projections or grooves includes two semi-circular projections centered around the second axis and disposed on opposite sides of the first insert. The fourth set of projections or grooves includes two semi-circular grooves centered around the second axis and disposed on opposite sides of the second insert. The semi-circular projections of the third set and semi-circular grooves of the fourth set are configured to cooperate to allow rotation of the second insert about the second axis.

The first and second annular projections or grooves are centered around and symmetrical about the third axis and are offset from diameters of the second insert and the femoral head.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which.

DETAILED DESCRIPTION OF THE DRAWINGS

Figure 1:
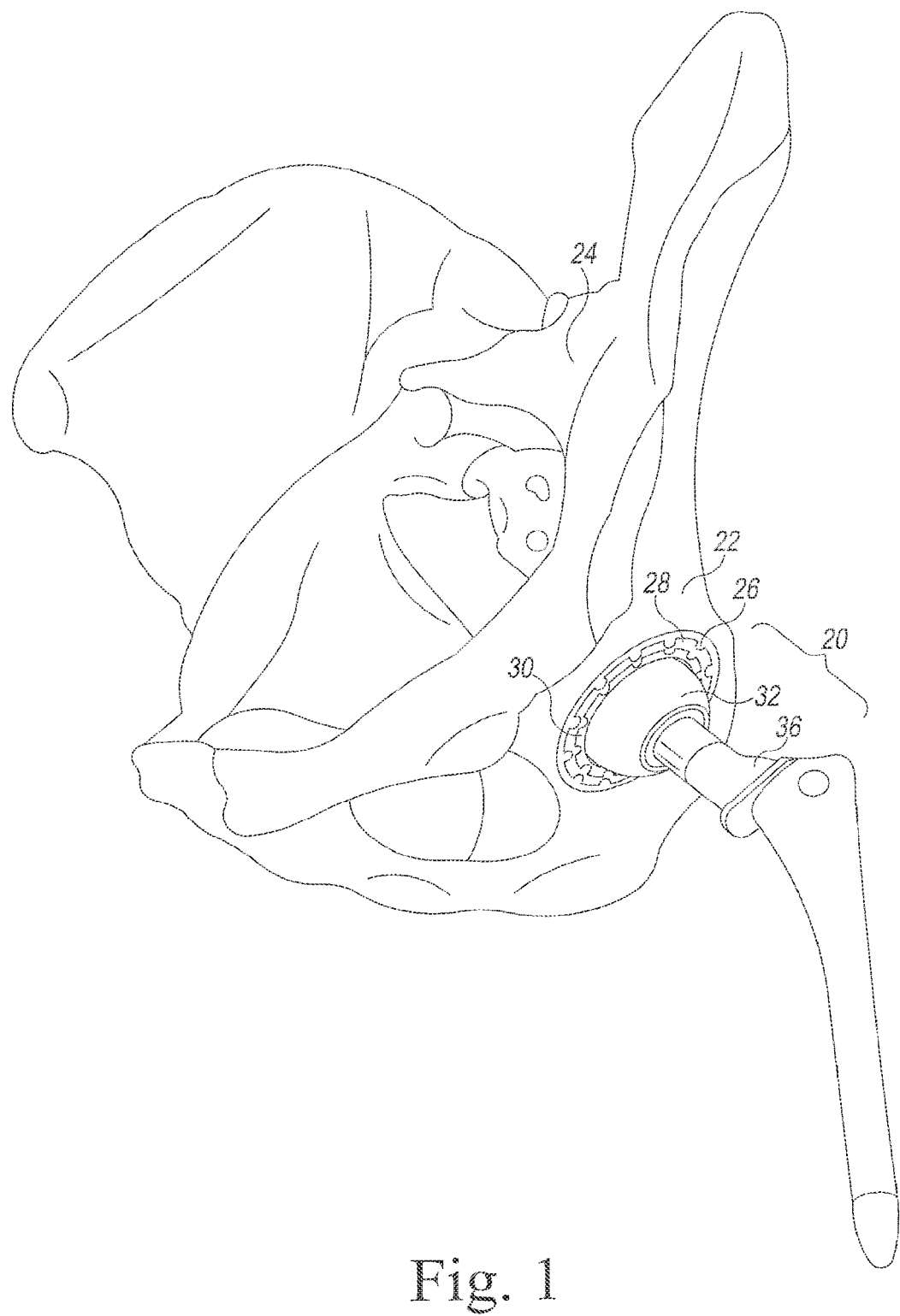
FIG. 1 is a perspective view of a first embodiment of an acetabular hip implant depicted within an acetabulum of a pelvic bone and further including a stem component extending from a femoral component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 2:
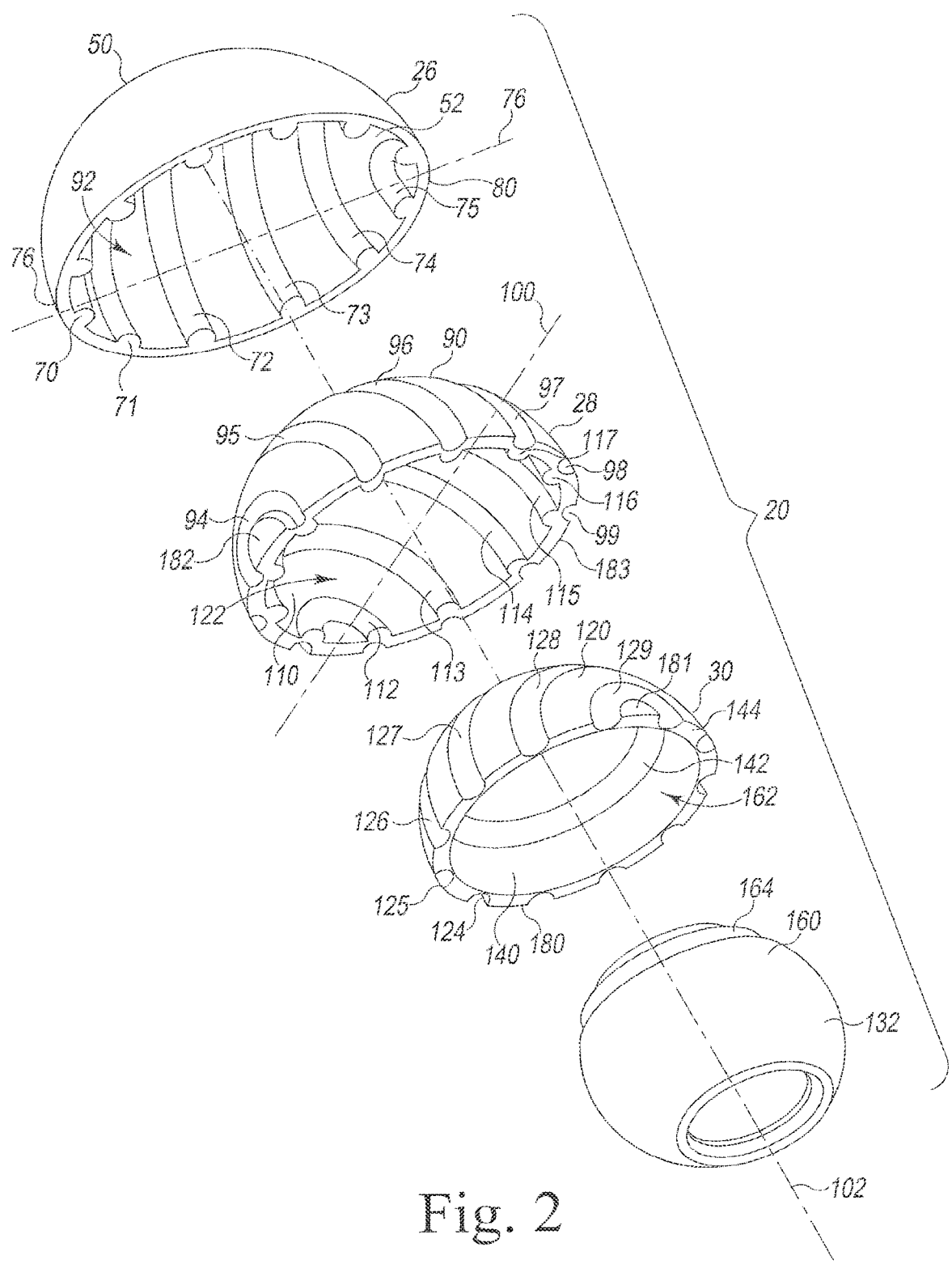
FIG. 2 is an exploded perspective view of the acetabular hip implant of FIG. 1.

Referring now to FIGS. 1 and 2, a first embodiment of an acetabular hip implant 20 is depicted within an acetabulum 22 of a human pelvic bone 24. The acetabular hip implant 20 generally includes an acetabular shell component 26, an inner insert 28, an outer insert 30, and a femoral head component 32. The acetabular shell component 26 is generally configured to be implanted within the acetabulum 22 of a patient, as seen in FIG. 1. The inner insert 28 is configured to be received within and secured to the acetabular shell component 26, the outer insert 30 is configured to be received within and secured to the inner insert 28, and the femoral head component 32 is configured to be received within and secured to the outer insert 30, as will be described in greater detail hereinafter. The femoral head component 32 is configured to be secured to a femoral stem 36, which is configured to be implanted in femoral bone tissue (not shown) of the patient.

As seen in FIGS. 1 and 2, the acetabular shell component 26 includes an outer surface 50 having a generally rounded shape that is hemispherical or at least partially spherical. The outer surface 50 is configured to be implanted within the acetabulum 22 using any method or structure known in the art. The acetabular shell component 26 further includes an inner surface 52 that is partially spherical in shape. In this embodiment, a plurality of semi-annular projections 70-75 is formed within the inner surface 52 of the acetabular shell component 26. Each of the semi-annular projections 70-75 has a center along an abduction axis 76 that allow the semi-annular projections 70-75 to cooperate with a feature within the inner insert 28 to allow rotation of the inner insert 28 with respect to the acetabular shell component 26 about the abduction axis 76, as will be discussed in greater detail below.

While six semi-annular projections 70-75 are depicted in FIG. 2, one or more projections 70-75 may be utilized. In one embodiment, two central projections 72, 73 or a single central projection (not shown) may be utilized. In another embodiment, only projections 70, 75 disposed at opposing axial ends 78, 80 of the acetabular shell component 26 may be utilized.

The inner insert 28, as best seen in FIG. 2, includes an outer surface 90 having a generally hemispherical or at least partially spherical shape and having a size that is slightly smaller than a size of the inner surface 52 of the acetabular shell component 26. The outer surface 90 of the inner insert 28 is configured to be received and secured within a cavity 92 formed by the inner surface 52 of the acetabular shell component 26. A plurality of semi-annular grooves 94-99 are formed within the outer surface 90 of the inner insert 28.

Due to the sizes and shapes of the acetabular shell component 26 and the inner insert 28, the semi-annular projections 70, 75, and the semi-annular grooves 94-99, the inner insert 28 will only fit within the acetabular shell component with the semi-annular projections 70-75 of the acetabular shell component 26 within the semi-annular grooves 94-99 of the inner insert 28. The semi-annular grooves 94-99 cooperate with respective semi-annular projections 70-75 in the inner surface 52 of the acetabular shell component 26 to allow the inner insert 28 to rotate relative to the acetabular shell component 26 about the abduction axis 76. In particular, the semi-annular projections 70-75 form a bearing surface along which the semi-annular grooves 94-99 ride during rotation of the inner insert 28.

While six grooves 94-99 are depicted in FIG. 2, any number of grooves 94-99 may be utilized so long as a number of the grooves 94-99 is the same as or greater than a number of the projections 70-75 within the acetabular shell component 26. Similarly, the locations of the projections 70-75 and grooves 94-99 must also correspond to allow insertion of each of the projections 70-75 into a corresponding groove 94-99.

While the acetabular shell component 26 is shown having projections 70-75 and the inner insert 28 is shown having grooves 94-99, such elements may be reversed to allow rotation of the inner insert 28 relative to the acetabular shell component 26 about the abduction axis 76.

In addition to allowing rotation about the abduction axis 76, the projections 70-75 and grooves 94-99 cooperate to prevent rotation of the inner insert 28 with respect to the acetabular shell component 26 about any other axes, including a flexion axis 100 and an axial axis 102. The abduction axis 76, in the embodiments shown herein, is orthogonal to the flexion axis 100 and the axial axis 102, and the flexion axis 100 is orthogonal to the axial axis 102. Optionally, the abduction axis 76, the flexion axis 100, and the axial axis 102 need not be orthogonal to one another.

Figure 4:
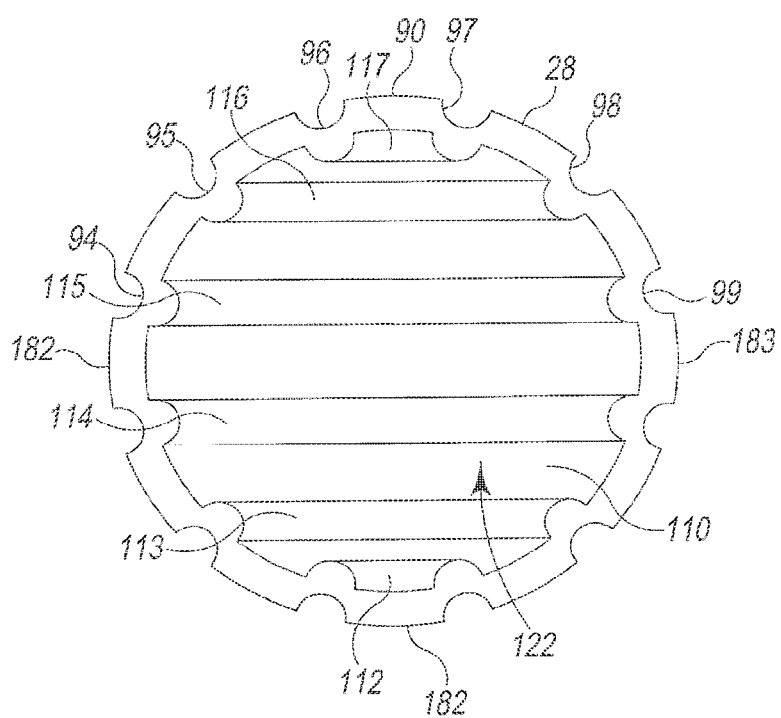
FIG. 4 is a plan view of an inner insert of the acetabular hip implant of FIG. 1.

Referring again to FIG. 4, the inner insert 28 further includes an inner surface 110 that is generally partially spherical in shape. A plurality of semi-annular projections 112-117 is defined in the inner surface 110 of the inner insert 28. Each of the semi-annular projections 112-117 has a center along the flexion axis 100 to allow the semi-annular projections 112-117 to cooperate with one or more feature(s) within the outer insert 30. The semi-annular projections 112-117 and the feature(s) within the outer insert 30 allow rotation of the outer insert 30 about the flexion axis 100, as will be discussed in greater detail below.

The outer insert 30 includes an outer surface 120 having a generally hemispherical or at least partially spherical shape and having a size that is slightly smaller than a size of a cavity 122 formed by the inner surface 110 of the inner insert 28. The outer surface 120 of the outer insert 30 is configured to be received and secured within the cavity 122. A plurality of semi-annular grooves 124-129 is defined in the outer surface 120 of the outer insert 30.

Due to the sizes and shapes of the inner and outer inserts 28, 30, the semi-annular projections 112-117, and the semi-annular grooves 124-129, the outer insert 30 will only fit within the inner insert 28 with the semi-annular projections 112-117 of the inner insert 28 within the semi-annular grooves 124-129 of the outer insert 30. The semi-annular projections 112-117 and respective semi-annular grooves 124-129 cooperate to allow rotation of the outer insert 30 with respect to the inner insert 28 about the flexion axis 100. In particular, the semi-annular projections 112-117 form a bearing surface along which the semi-annular grooves 124-129 ride during rotation of the outer insert 30.

The outer insert 30 further includes an inner surface 140 that is generally partially spherical in shape. The outer insert 30 includes an annular projection 142 spaced inwardly from an outer edge 144 of the outer insert 30 and which is symmetrical about the axial axis 102. The function of the annular projection 142 will be discussed in greater detail below.

Still referring to FIG. 2, the femoral head component 32 includes an outer surface 160 having a generally spherical shape and having a size that is slightly smaller than the size of a cavity 162 formed by the inner surface 140 of the outer insert 30. The femoral head component 32 is configured to be received by and secured within the cavity formed by the inner surface 140 of the outer insert 30. The outer surface 160 of the femoral head component 32 further includes an annular groove 164 opposite the femoral stem 36, symmetrical about the axial axis 102, and offset from a diameter of the femoral head component 32. The femoral head component 32 is configured to fit within the outer insert 30, such that the annular projection 142 of the outer insert 30 snaps into the annular groove 164 of the femoral head 32.

When the acetabular hip implant 20 is assembled, the femoral head component 32 rotates with respect to the outer insert 30 about the axial axis 102 with the annular projection 142 providing a bearing surface along which the annular groove 164 rides. This configuration prevents rotation of the femoral head 32 with respect to the outer insert 30 about the abduction axis 76 and the flexion 100 axis.

While the femoral head component 32 is shown with an annular groove 164 and the outer insert 30 is shown with an annular projection 142, in an alternative embodiment, the femoral head component 32 may include an annular projection and the outer insert 30 may include an annular groove.

Figure 3:
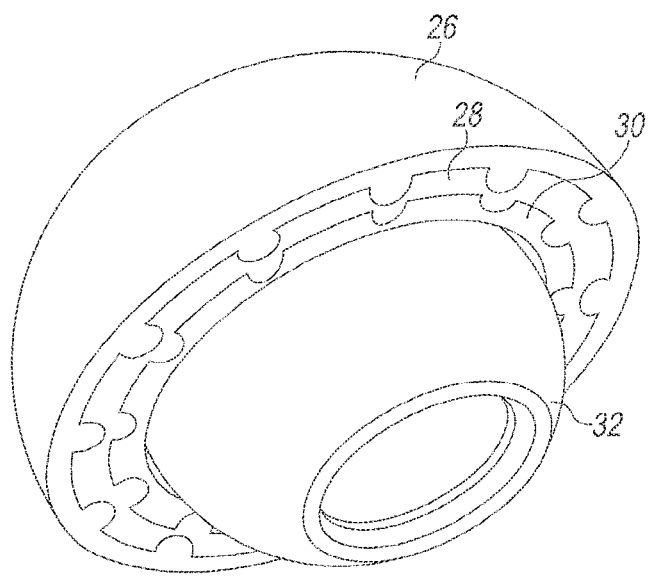
FIG. 3 is a perspective view of the acetabular hip implant of FIG. 1.

Referring to FIGS. 1-3, when the acetabular hip implant 20 is assembled, the inner insert 28 is secured for rotation about the abduction axis 76 within the acetabular shell component 26, the outer insert 30 is secured for rotation about the flexion axis 100 within the inner insert 28, and the femoral head component 32 is secured for rotation about the axial axis 102 within the outer insert 30. This arrangement mechanically constrains the acetabular hip implant 20, thus preventing dislocation of the femoral head component 32 during movement.

When the annular projection 142 of the outer insert 30 is disposed within the annular groove 164 of the femoral head component 32, the femoral head component 32 cannot be removed from the outer insert 30 without a great amount of force and/or use of a tool. The femoral head component 32 is therefore mechanically constrained to prevent dislocation of the femoral head component 32 from the outer insert 30.

As noted above, the semi-annular projections 112-117 and the semi-annular grooves 124-129 of the inner and outer inserts 28, 30, respectively, allow rotation about the flexion axis 100 with an angle of rotation of about 90 degrees. The semi-annular projections 112-117 and the semi-annular grooves 124-129 therefore have a dual function of restricting rotation of the outer insert 30 within the inner insert 28 and preventing complete dislocation of the outer insert 30 from the inner insert 28. Specifically, with respect to dislocation, semi-circular lips 180, 181 forming a portion of the semi-annular grooves 124, 129 interfere with the semi-annular projections 112, 117 to prevent movement of the outer insert 30 out of the inner insert 28. When force is exerted on the outer insert 30 (for example, by way of the femoral head component 32 and/or femoral stem 36), the lips 181, 182 interfere with the semi-annular projections 112, 117, respectively, to prevent dislocation.

Similarly, the semi-annular projections 70-75 and the semi-annular grooves 94-99 of the acetabular shell component 26 and the inner insert 28, respectively, allow rotation about the abduction axis 76 with an angle of rotation of about 90 degrees. The semi-annular projections 70-75 and the semi-annular grooves 94-99 therefore have a dual function of restricting rotation of the inner insert 28 within the acetabular shell component 26 and preventing complete dislocation of the inner insert 28 from the acetabular shell component 26. In particular, with respect to dislocation, semi-circular lips 182, 183 forming a portion of the semi-annular grooves 94, 99 interfere with the semi-annular projections 70, 75, respectively, to prevent movement of the inner insert 28 out of the acetabular shell component 26. When force is exerted on the inner insert 28 (for example, by way of the outer insert 30, the femoral head component 32, and/or the femoral stem 36), the lips 182, 183 interfere with the semi-annular projections 70, 75, respectively, to prevent dislocation.

The mechanisms for restricting rotation of the inner insert 28, the outer insert 30, and the femoral head component 32 combine to constrain the femoral head component 32 and prevent dislocation of the femoral head component 32 alone or in combination with the outer insert 30 and/or the inner insert 28.

Figure 5:
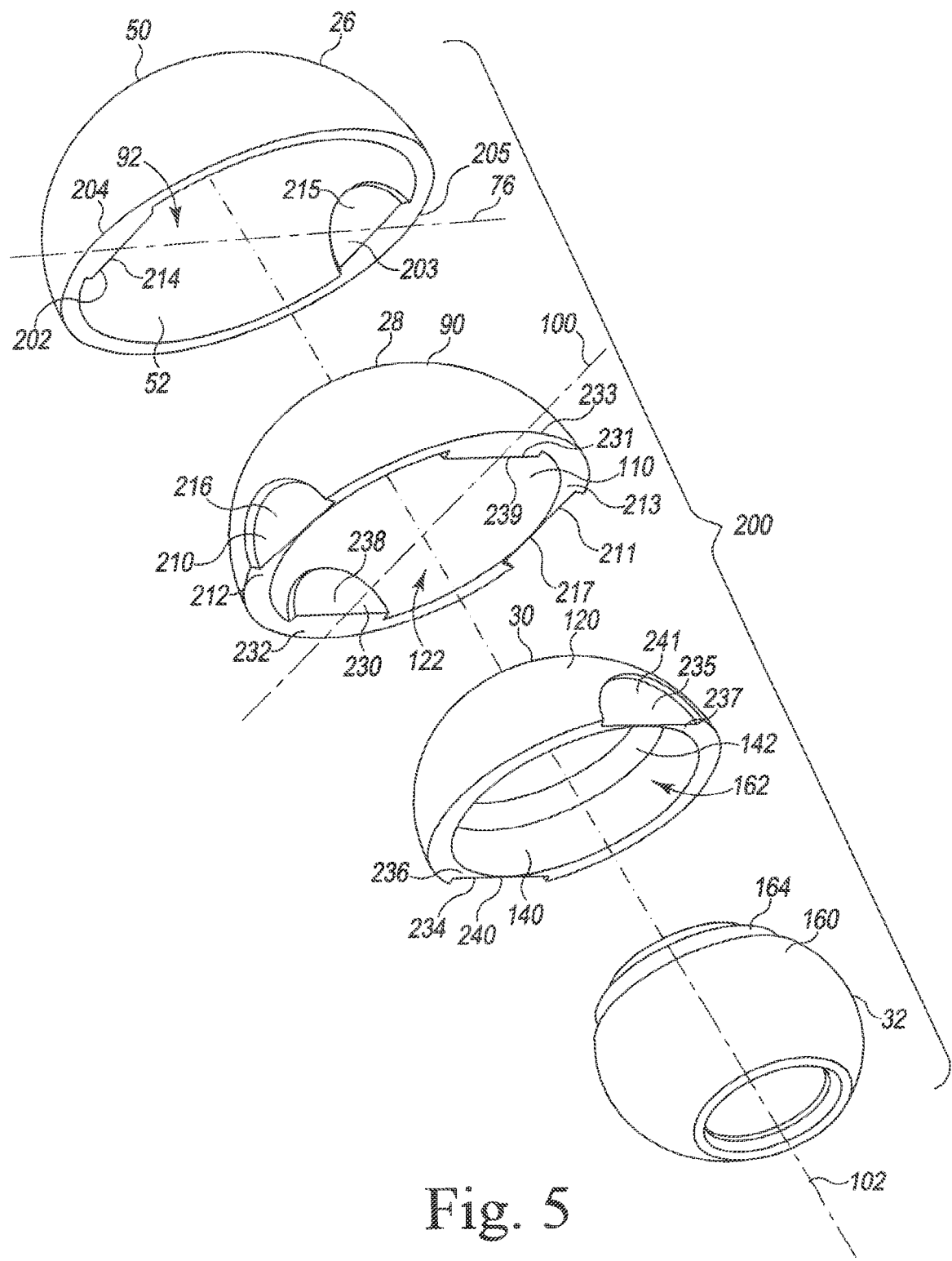
FIG. 5 is an exploded perspective view of a second embodiment of an acetabular hip implant.
Figure 6:
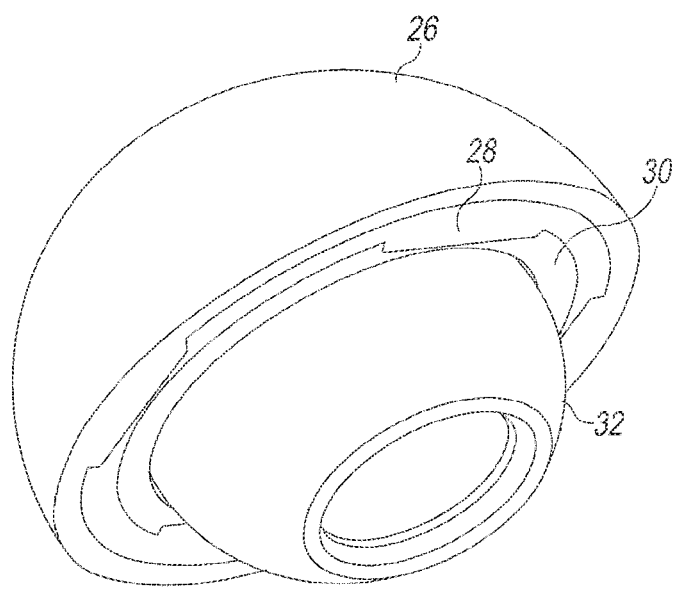
FIG. 6 is a perspective view of the acetabular hip implant of FIG. 4.

It will be appreciated that the principles of the present disclosure and at least some of the benefits may be carried out in a number of different ways. For example, FIGS. 5 and 6 depict an alternative embodiment of an acetabular hip implant 200. The acetabular hip implant 200 is similar to the acetabular hip implant of FIGS. 1-4 and, thus, only the differences will be described. As best seen in FIG. 5, a set of semi-circular projections 202, 203 is defined in opposing sides 204, 205 of the inner surface 52 of the acetabular shell component 26. The semi-circular projections 202, 203 in this embodiment, are generally perpendicular to the abduction axis 76. The semi-circular projections 202, 203 are also parallel to each other. The function of the semi-circular projections 202, 203 will be described in greater detail below.

A set of semi-circular grooves 210, 211 is defined in opposing sides 212, 213 of the outer surface 90 of the inner insert 28. The semi-circular grooves 210, 211 are generally perpendicular to the abduction axis 76 and are parallel to one another.

The inner insert 28 only fits within the cavity 92 formed by the acetabular shell component 26 with the set of semi-circular projections 202, 203 disposed within the set of semi-circular grooves 210, 211 such that inner surfaces 214, 215 of the semi-circular projections 202, 203 are in contact with outer surfaces 216, 217 the semi-circular grooves 210, 211. The contact between the inner surfaces 214, 215 and outer surfaces 217 provides a bearing surface for rotation of the inner insert 28 with respect to the acetabular shell component 26 about the abduction axis 76. This arrangement also prevents rotation of the inner insert 28 relative to the acetabular shell component 26 about any other axis, including about the flexion axis 100 and/or the axial axis 102.

Still referring to FIG. 5, a set of semi-circular projections 230, 231 is defined in opposing sides 232, 233 of the inner surface 110 of the inner insert 28. The semi-circular projections 230, 231 in this embodiment, are generally perpendicular to the flexion axis 100 and parallel to one another. The function of the semi-circular projections 230, 231 will be discussed in greater detail below.

A set of semi-circular grooves 234, 235 is defined in opposing sides 236, 237 of the outer surface 120 of the outer insert 30. The semi-circular grooves 234, 235 are generally perpendicular to the flexion axis 100 and parallel to one another.

The outer insert 30 only fits within the cavity 122 formed by the inner insert 28 with the set of semi-circular projections 230, 231 disposed within the set of semi-circular grooves 234, 235 such that inner surfaces 238, 239 of the semi-circular projections 230, 231 are in contact with outer surfaces 240, 241 of the semi-circular grooves 234, 235. The contact between the inner surfaces 238, 239 and the outer surfaces 240, 241 provides a bearing surface for rotation of the outer insert 30 with respect to the inner insert 28 about the flexion axis 100. This arrangement also prevents rotation of the outer insert 30 relative to the inner insert 28 about any other axis including the abduction axis 76 and/or the axial axis 102.

The outer insert 30 of the embodiment of FIGS. 5 and 6 includes an annular projection 142 and the femoral head component 32 includes an annular groove 164, as described in detail with respect to FIG. 2. The functionality of the annular projection 142 and annular groove 164 is also the same as described with respect to the first embodiment.

Similar to the first embodiment, when the acetabular hip implant 20 is assembled, the inner insert 28 is secured for rotation about the abduction axis 76 within the acetabular shell component 26, the outer insert 30 is secured for rotation about the flexion axis 100 within the inner insert 28, and the femoral head component 32 is secured for rotation about the axial axis 102 within the outer insert 30. This arrangement mechanically constrains the acetabular hip implant 20, thus preventing dislocation of the femoral head component 32 during movement.

When the annular projection 142 of the outer insert 30 is disposed within the annular groove 164 of the femoral head component 32, the femoral head component 32 cannot be removed from the outer insert 30 without a great amount of force and/or use of a tool. The femoral head component 32 is therefore mechanically constrained to prevent dislocation of the femoral head component 32 from the outer insert 30.

As noted above, the semi-circular projections 230, 231 and the semi-circular grooves 234, 235 of the inner and outer inserts 28, 30, respectively, allow rotation about the flexion axis 100 with an angle of rotation of about _____ degrees. The semi-circular projections 230, 231 and the semi-circular grooves 234, 235 therefore have a dual function of restricting rotation of the outer insert 30 within the inner insert 28 and preventing complete dislocation of the outer insert 30 from the inner insert 28. Specifically, with respect to dislocation, semi-circular projections 230, 231 interfere with edges forming the semi-circular grooves 234, 235 to prevent dislocation of the outer insert 30 from the inner insert 28.

Similarly, the semi-circular projections 202, 203 and the semi-circular grooves 210, 211 of the acetabular shell component 26 and the inner insert 28, respectively, allow rotation about the abduction axis 76 with an angle of rotation of about _____ degrees. The semi-circular projections 202, 203 and the semi-circular grooves 210, 211 therefore have a dual function of restricting rotation of the inner insert 28 within the acetabular shell component 26 and preventing complete dislocation of the inner insert 28 from the acetabular shell component 26. In particular, with respect to dislocation, the semi-circular projections 202, 203 interfere with edges forming the semi-circular grooves 210, 211 to prevent dislocation of the inner insert 28 from the acetabular shell component 26.

The mechanisms for restricting rotation of the inner insert 28, the outer insert 30, and the femoral head component 32 therefore combine to constrain the femoral head component 32 and prevent dislocation of the femoral head component 32 alone or in combination with the outer insert 30 and/or the inner insert 28.

The acetabular shell component 26 of any of the acetabular hip implants disclosed herein may be formed of any combination of metal, ultra-high molecular weight polyethylene (UHMWPE), ceramic, polyetheretherketone (PEEK), or any other materials known in the art. In one exemplary embodiment, the acetabular shell component 26 includes a metal shell having an inner surface lined with a polymeric material (or a separate polymeric component attached to the metal shell). The polymeric material may be an ultra-high molecular weight polyethylene (UHMWPE) and the metal may be a higher hardness alloy, such as an alloy of cobalt and chromium, for example CoCrMo. The polymeric insert may be locked, molded, or otherwise secured to the metal shell. In another example, the acetabular shell component 26 has a metal shell with an external surface that is provided with a coating that promotes ingrowth of bone tissue. For example, the external surface of the metal shell may have a porous structure, for example, a coating of cobalt-chromium alloy beads, such as a product sold by DePuy Orthopaedics Inc. under the trade mark POROCOAT®. Optionally, the external surface of the metal shell may be provided with a coating of an additional or alternative material that promotes bone ingrowth, such as a hydroxyapatite material.

Although the axes 76, 100, 102 are described as aligning with the anatomical axes (i.e., abduction, flexion, axial), the axes 76, 100, 102 may alternatively be aligned in another manner, so long as the axes 76, 100, 102 are orthogonal to one another. Optionally, the abduction axis 76, the flexion axis 100, and the axial axis 102 need not be orthogonal to one another.

The acetabular hip implants disclosed herein allow the three basic motions of the hip to be broken down into three different movements. The combined rotational capabilities of these three different movements, namely, movement of the inner insert 28 with respect to the shell 26 about the abduction axis 76, movement of the outer insert 30 with respect to the inner insert 28 about the flexion axis 100, and movement of the femoral head component 32 with respect to the outer insert 30 about the axial axis 102, provides a large range of motion of the femoral head component 32 relative to the acetabular shell component 26. The embodiments disclosed and described in detail herein provide this large range of motion in a manner that prevents dislocation of any of the components of the acetabular hip implant.

While two inserts 28, 30 are depicted in the figures herein, it should be understood that a single insert 28 or 30 may be utilized.

In an exemplary implementation, the acetabular implant 20 is used in a total hip replacement procedure. A surgical method for implanting the acetabular hip implant 20 of FIGS. 1 and 2 involves assembling the components 26, 28, 30, and 32 of the acetabular hip implant 20 and implanting the acetabular hip implant 20 within the acetabulum 22 of the patient while supporting the femoral stem 36 within the femoral bone tissue.

In further detail, a reamer, not shown, is typically used to ream or otherwise cut the acetabulum 22 in order to form a hemispherically shaped cavity. The surgeon may then implant either final components or trial fit components. Trial fitting is well known in the art and assists the surgeon in final preparation of the acetabulum and in choosing the proper sizes of the various components of the acetabular hip implant 20.

After suitable trial fitting, the trial implant is removed and the surgeon may then implant the acetabular shell component 26 into the acetabulum 22. The acetabular shell component 26 may be press fit, bolted, cemented or otherwise attached to the acetabulum 22, as is well known in the art.

In a first exemplary procedure, the acetabular shell component 26 is implanted into the acetabulum 22 separately and then the inner insert 28 is pressed into the acetabular shell component 26 in vivo. The inner insert 28 is aligned with the acetabular shell component 26 such that the semi-annular projections 70-75 or semi-circular projections 202, 203 of the acetabular shell component 26 are received within the semi-annular grooves 94-99 or semi-circular grooves 210, 211 of the inner insert 28 to allow rotation of the inner insert 28 with respect to the acetabular shell component 26 about the abduction axis 76. The acetabular shell component 26 is therefore stationary and the inner insert 28 rotates about the abduction axis 76.

The outer insert 30 is pressed into the inner insert 28 in vivo. Optionally, the outer insert 30 may be pressed into the inner insert 28 external to the acetabulum 22. As noted above, the outer insert 30 is aligned with the inner insert 28 such that the semi-annular projections 112-117 or semi-circular projections 230, 231 of the inner insert 28 are received within the semi-annular grooves 124-129 or semi-circular grooves 234, 235 of the outer insert 30 to allow rotation of the outer insert 30 with respect to the inner insert 28 about the flexion axis 100. The inner insert 28 is therefore stationary with respect to the flexion axis 100.

Once the inner and outer inserts 28, 30 are secured, the surgeon secures the femoral head component 32 within the outer insert 30. The femoral stem 36 may already be implanted within the femoral bone tissue or may be implanted within the femoral bone tissue after the femoral head component 32 is secured within the outer insert 30. To secure the femoral head component 32 within the outer insert 30, the femoral head component 32 is pressed into the outer insert 30 until the annular projection 142 of the outer insert 30 snaps into the annular groove 164 of the femoral head component 32. The positioning and shape of the projection 142 and the groove 164 allow the femoral head component 32 to rotate with respect to the outer insert 30 about the axial axis 102. The outer insert 30 is therefore stationary with respect to the axial axis 102.

In the embodiment described above, the components of the acetabular hip implant 20 are assembled in vivo. Alternatively, any of the components (or all) may instead be assembled external to the acetabulum 22 prior to implantation. In addition or alternatively, one skilled in the art should understand that the same steps may be utilized (minus insertion of the outer insert 30 into the inner insert 28) if the outer insert 30 is omitted.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An acetabular hip implant, comprising:
an acetabular shell component configured to be implanted into an acetabulum of a patient, the acetabular shell having an inner surface, a first inner feature defined on the inner surface, and a second inner feature, separate from the first inner feature, defined on the inner surface opposite from and parallel to the first inner feature, wherein the first and second inner features define a first axis of rotation;
a first insert having an inner surface and an outer surface, wherein the first insert is received in the acetabular shell component such that the outer surface of the first insert is in contact with the inner surface of the acetabular shell, the first insert having (i) a first outer feature defined on the outer surface of the first insert and coupled with the first inner feature of the acetabular shell, (ii) a second outer feature, separate from the first outer feature, defined on the outer surface of the first insert and coupled with the second inner feature of the acetabular shell, (iii) a third inner feature defined on the inner surface of the first insert, and (iv) a fourth inner feature, separate from the third inner feature, defined on the inner surface of the first insert opposite from and parallel to the third inner feature, wherein the third and fourth inner features define a second axis of rotation orthogonal to the first axis of rotation; and
a second insert having an inner surface and an outer surface, wherein the second insert is received in the first insert such that the outer surface of the second insert is in contact with the inner surface of the first insert, the second insert having (i) a third outer feature defined on the outer surface of the second insert and coupled with the third inner feature of the first insert, (ii) a fourth outer feature, separate from the third outer feature, defined on the outer surface of the second insert and coupled with the fourth inner feature of the first insert, and (iii) a fifth inner feature defined on the inner surface of the second insert, wherein the fifth inner feature defines a third axis of rotation of a femoral head when the femoral head is received in the second insert, wherein the third axis of rotation is orthogonal to the first and second axes of rotation.

2. The acetabular hip implant of claim 1, wherein the first inner feature, the second inner feature, the first outer feature, and the second outer feature cooperate to limit the rotation of the first insert to the first axis of rotation, and wherein the third inner feature, the fourth inner feature, the third outer feature, and the further outer feature cooperate to limit the rotation of the second insert to the second axis of rotation, and wherein the fifth inner feature limits the rotation of the femoral head to the third axis of rotation.

3. The acetabular hip implant of claim 1, wherein each of the first, second, third, and fourth inner features has a similar shape, and wherein each of the first, second, third, and fourth outer features has a similar shape.

4. The acetabular hip implant of claim 1, wherein the first inner feature is different from the first outer feature, the second inner feature is different from the second outer feature, the third inner feature is different from the third outer feature, and the fourth inner feature is different from the fourth outer feature.

5. The acetabular hip implant of claim 1, wherein each of the first, second, third, and fourth inner features comprises semi-circular projections, and wherein each of the first, second, third, and fourth outer features comprises semi-circular grooves.

6. The acetabular hip implant of claim 1, wherein each of the first, second, third, and fourth inner features comprises semi-circular grooves, and wherein each of the first, second, third, and fourth outer features comprises semi-circular projections.

7. The acetabular hip implant of claim 1, wherein the fifth inner feature comprises an annular groove defined in the inner surface of the second insert.

8. The acetabular hip implant of claim 1, wherein the fifth inner feature comprises an annular projection defined on the inner surface of the second insert.

9. The acetabular hip implant of claim 1, further comprising the femoral head, wherein the femoral head having an outer surface, wherein the femoral head is received in the second insert such that the outer surface of the femoral head is in contact with the inner surface of the second insert, the femoral head having a sixth feature defined on the outer surface of the femoral head and coupled with the fifth inner feature of the second insert.

10. An acetabular hip implant, comprising:
an acetabular shell component configured to be implanted into an acetabulum of a patient, the acetabular shell having an inner surface, a first inner feature defined on the inner surface, and a second inner feature, separate from the first inner feature, defined on the inner surface opposite from and parallel to the first inner feature, wherein the first and second inner features define a first axis of rotation;
a first insert having an inner surface and an outer surface, wherein the first insert is configured to be received in the acetabular shell component such that, when received in the acetabular shell component, the outer surface of the first insert contacts the inner surface of the acetabular shell, the first insert having (i) a first outer feature defined on the outer surface of the first insert and configured to couple with the first inner feature of the acetabular shell, (ii) a second outer feature, separate from the first outer feature, defined on the outer surface of the first insert and configured to couple with the second inner feature of the acetabular shell, (iii) a third inner feature defined on the inner surface of the first insert, and (iv) a fourth inner feature, separate from the third inner feature, defined on the inner surface of the first insert opposite from and parallel to the third inner feature, wherein the third and fourth inner features define a second axis of rotation orthogonal to the first axis of rotation;
a second insert having an inner surface and an outer surface, wherein the second insert is configured to be received in the first insert such that, when received in the first insert, the outer surface of the second insert contacts the inner surface of the first insert, the second insert having (i) a third outer feature defined on the outer surface of the second insert and configured to couple with the third inner feature of the first insert, (ii) a fourth outer feature, separate from the third outer feature, defined on the outer surface of the second insert and configured to couple with the fourth inner feature of the first insert, and (iii) a fifth inner feature defined on the inner surface of the second insert; and
a femoral head having an outer surface, wherein the femoral head is configured to be received in the second insert such that, when received in the second insert, the outer surface of the femoral head contacts the inner surface of the second insert, the femoral head having a sixth feature defined on the outer surface of the femoral head and configured to couple with the fifth inner feature of the second insert.

11. The acetabular hip implant of claim 10, wherein the fifth inner feature of the second insert defines a third axis of rotation of the femoral head when the femoral head is received in the second insert, and wherein the third axis of rotation is orthogonal to the first and second axes of rotation.

12. The acetabular hip implant of claim 10, wherein the fifth inner feature comprises an annular groove defined in the inner surface of the second insert and the sixth inner feature comprises an annular projection defined on the outer surface of the femoral head.

13. The acetabular hip implant of claim 10, wherein the fifth inner feature comprises an annular projection defined in the inner surface of the second insert and the sixth inner feature comprises an annular groove defined on the outer surface of the femoral head.

14. The acetabular hip implant of claim 10, wherein the first inner feature, the second inner feature, the first outer feature, and the second outer feature cooperate to limit the rotation of the first insert to the first axis of rotation, and wherein the third inner feature, the fourth inner feature, the third outer feature, and the further outer feature cooperate to limit the rotation of the second insert to the second axis of rotation, and wherein the fifth inner feature limits the rotation of the femoral head to the third axis of rotation.

15. The acetabular hip implant of claim 10, wherein each of the first, second, third, and fourth inner features has a similar shape, and wherein each of the first, second, third, and fourth outer features has a similar shape.

16. The acetabular hip implant of claim 10, wherein the first inner feature is different from the first outer feature, the second inner feature is different from the second outer feature, the third inner feature is different from the third outer feature, and the fourth inner feature is different from the fourth outer feature.

17. The acetabular hip implant of claim 10, wherein each of the first, second, third, and fourth inner features comprises semi-circular projections, and wherein each of the first, second, third, and fourth outer features comprises semi-circular grooves.

18. The acetabular hip implant of claim 10, wherein each of the first, second, third, and fourth inner features comprises semi-circular grooves, and wherein each of the first, second, third, and fourth outer features comprises semi-circular projections.

* * * * *